Figure 1:
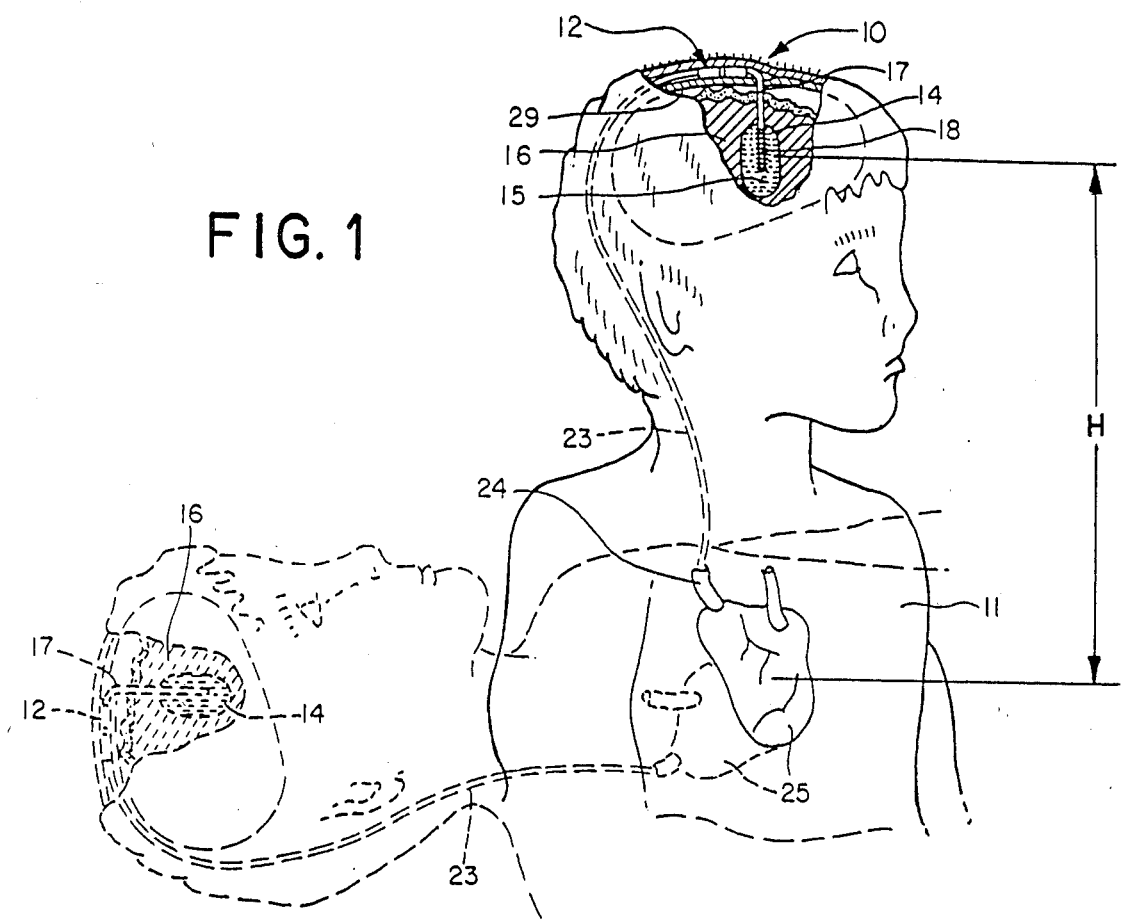
Figure 2:
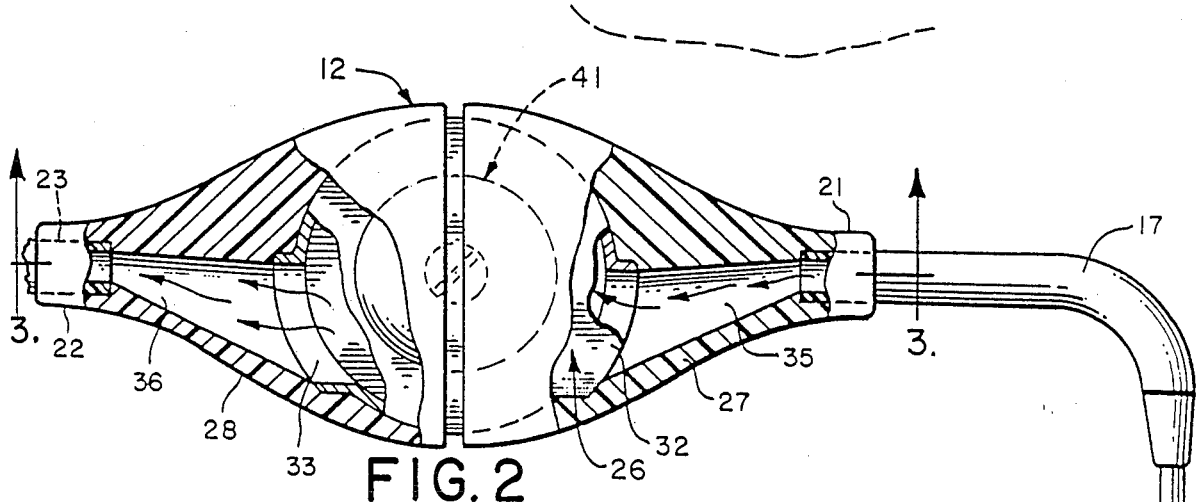

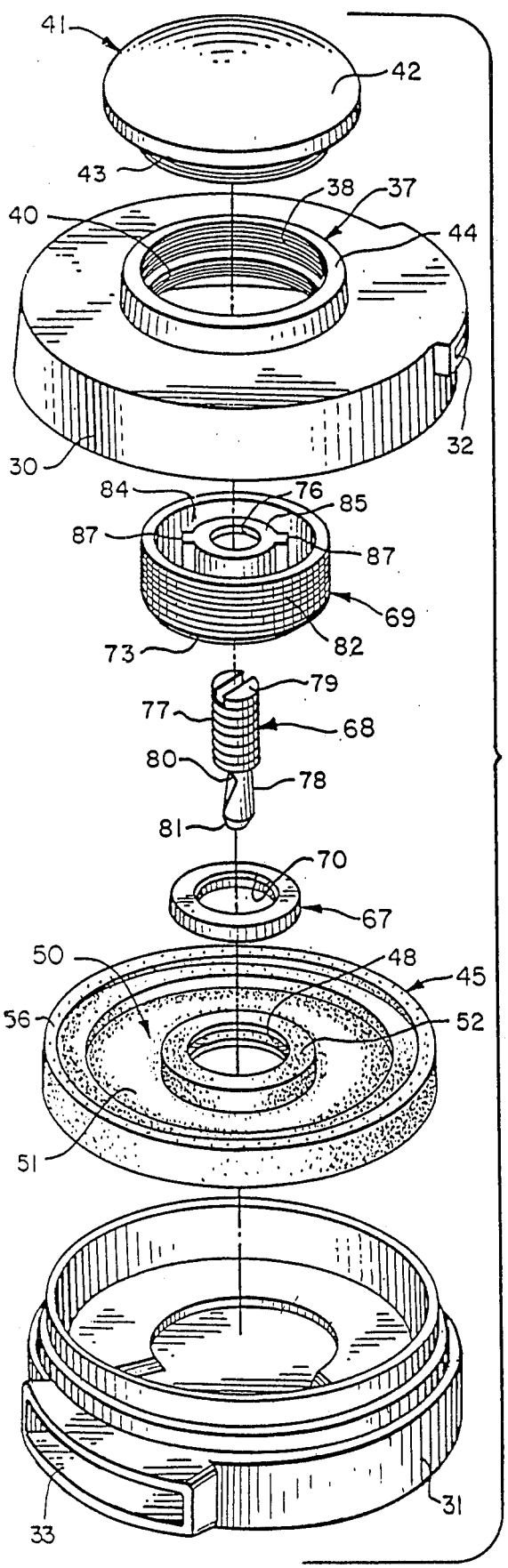
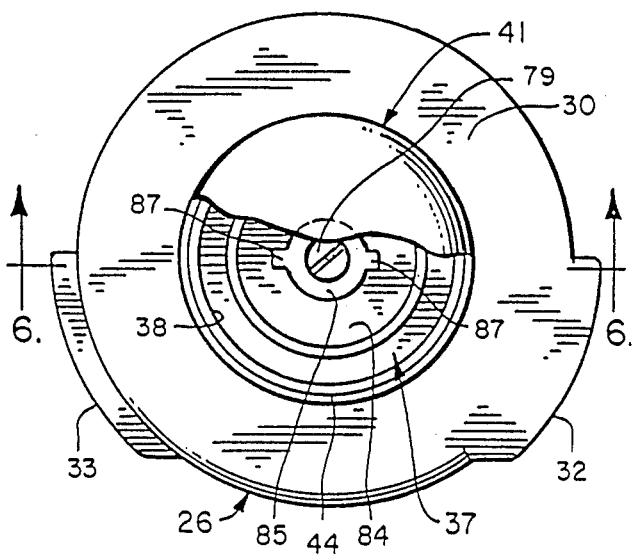
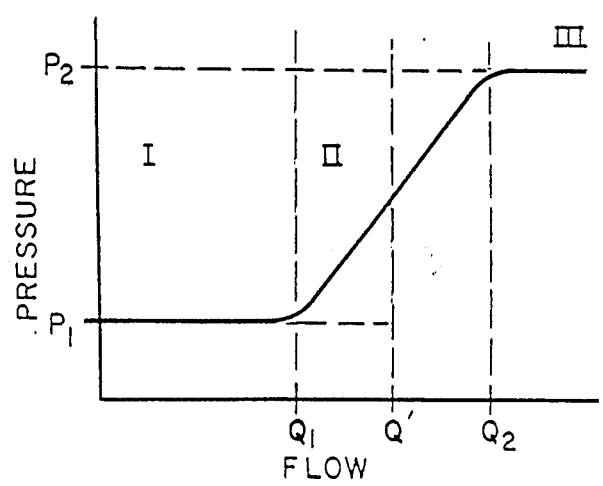

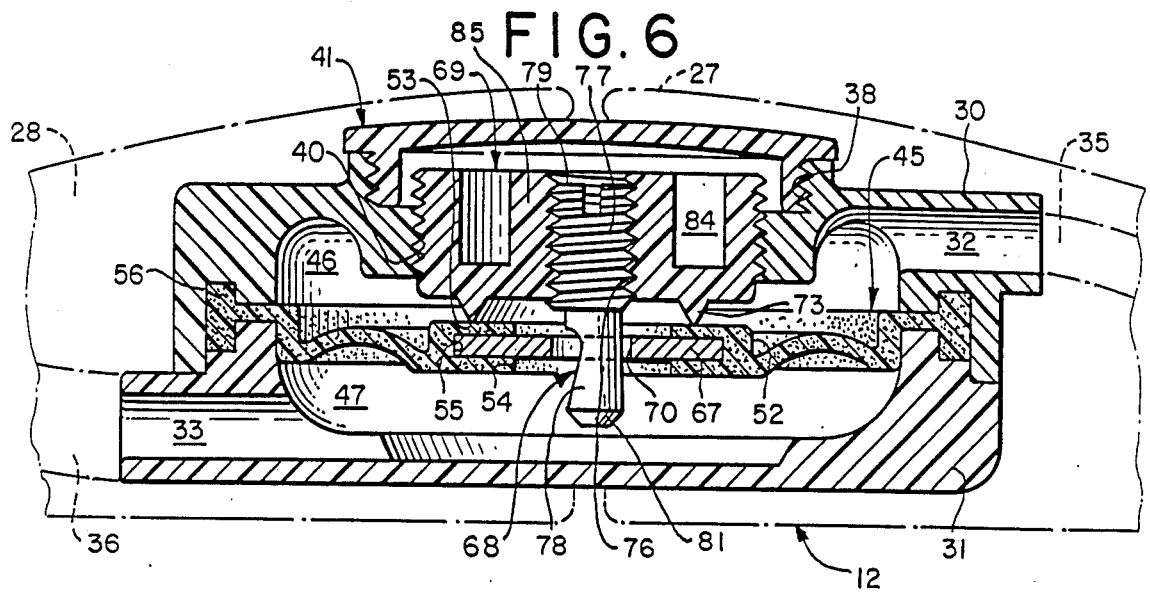

THREE STAGE IMPLANTABLE FLOW CONTROL VALVE WITH IMPROVED VALVE CLOSURE MEMBER

BACKGROUND OF THE INVENTION

The present invention relates to an intracranial CSF fluid control valve and, more particularly, to a three stage CSF valve having an adjustable valve stem member which establishes the pressure levels at which the valve transitions from a first constant pressure mode to a flow control mode, and from the flow control mode to a second constant pressure mode, and an adjustable valve closure member of improved construction which establishes valve opening pressure.

Hydrocephalus is a condition in which the body, for any one of a variety of reasons, is unable to relieve itself of excess cerebrospinal fluid (CSF) collected in the ventricles of the brain. The excessive collection of CSF in the ventricles results in an abnormal increase in epidural and intradural pressures, which may cause a number of adverse physiological effects including compression of the brain tissue, impairment of blood flow in the brain tissue, and impairment of the brain's normal metabolism.

Treatment of a hydrocephalic condition frequently involves relieving the abnormally high intracranial pressure. To this end, a variety of CSF pressure relief valves and methods of controlling CSF pressure have been developed which include various check valves, servo valves, or combinations thereof. Generally, such valves serve to divert CSF from the ventricles of the brain through a discharge line to a suitable drainage location in the body, such as the venous system or the peritoneal cavity, and, in their simplest form, operate by opening when the difference between CSF pressure and pressure in the discharge line exceeds a predetermined level.

The use of a differential pressure regulator in the treatment of hydrocephalus is potentially disadvantageous since it is possible for such a valve to open in response to a sudden, but nevertheless perfectly normal, increase in differential pressure between CSF in the ventricular spaces and fluid at the drainage location, resulting in abnormal and potentially dangerous hyperdrainage of the ventricular spaces. For example, when a patient stands after lying in a recumbent position, the resulting increased vertical height of the fluid column existing between the head and the drainage location may result in such an increase in differential pressure. Accordingly, three stage CSF pressure relief valves, such as that described in the copending application of Christian Sainte-Rose and Michael D. Hooven, entitled "Three Stage Valve", Ser. No. 672,868, filed Nov. 19, 1984, have been developed which serve to prevent undesired hyperdrainage by controlling the flow rate of fluid through the valve when a sudden increase in differential pressure occurs.

In a valve of preferred construction incorporating the present invention a diaphragm is movable in response to the pressure differential between ventricular CSF pressure in an inlet chamber on one side of the diaphragm, and the pressure of fluid at the drainage location in an outlet chamber on the other side of the diaphragm. The diaphragm includes a valve seat which is mounted concentrically thereon and which includes a fluid metering orifice. The diaphragm is arranged to engage an adjustable annular valve closure member in the inlet chamber so as to close the valve when the pressure differential falls below a predetermined minimum level. A valve stem extends through the orifice to provide in cooperation with the orifice fluid metering between the two chambers.

The motion of the diaphragm in response to changes in differential pressure between the two valve chambers causes the valve to progress through four valving conditions. In the first valving condition, the diaphragm engages the valve closure member to prevent fluid flow through the valve. In the second valving condition, when the pressure differential between the two chambers exceeds a minimum threshold level, fluid flow between the chambers is regulated by coaction between the valve seat and the valve stem to maintain a first predetermined pressure level in the inlet chamber. In the third valving condition, which occurs in response to a sudden further increase in differential pressure beyond a further threshold level, such as might be caused by a drastic change in the position of the patient, such as movement from a recumbent position to a vertical position, the valve seat and valve stem coact to maintain a controlled flow rate. In the fourth valving condition, where the pressure differential increases still further and exceeds a maximum threshold level, the valve seat and valve stem coact to maintain a second predetermined pressure differential to prevent hyperdrainage.

A CSF pressure relief valve is typically miniaturized for implantation and is required to perform with a high degree of precision under highly demanding conditions throughout a rather extensive, ever-changing mode of operation. Consequently, it has been necessary to carefully control the dimensions of the various parts of the valve, particularly the valve seat, the valve stem and the orifice defined by the valve seat. The parts involved are quite small, and working tolerances on the order of .0001 of an inch must be met. Considerable difficulty may be incurred in manufacturing such a valve, and it is to the reduction of this manufacturing difficulty that the construction of the present invention is directed.

A CSF pressure relief valve incorporating a one piece valve stem is described in U.S. Pat. No. 4,627,832, entitled "Three Stage Intracranial Pressure Relief Valve Having Single-Piece Valve Stem" which issued to Michael D. Hooven, et al. on Dec. 9, 1986. Alternative constructions for the valve members are described in the copending application of Michael D. Hooven, entitled "Three Stage Intracranial Pressure Control Valve", Ser. No. 812,779, filed Dec. 23, 1985 and in the copending application of Demetrios Doumenis, entitled "Three Stage Implantable Pressure Relief Valve with Adjustable Valve Stem Member", Ser. No. 812,780, filed Dec. 23, 1985.

The present invention is directed to an improvement in multi-stage CSF valve construction, and particularly in the valve closure member of such a valve. Basically, this improvement provides an annular valving surface on the valve closure member, which surface coacts with the diaphragm to provide positive control of fluid flow. By reason of the circumferential surface providing flow control, only a small movement of the diaphragm is necessary to condition the valve from a closed valving condition to an pen valving condition.

In view of the foregoing, it is a general object of the present invention to provide a new and improved valve for relieving intracranial pressure caused by the presence of excess CSF in the ventricles of the brain.

den pressure increases, as well as other intracranial pressure variations which may be encountered in a patient.

The internal construction and operation of the three stage valve of the invention may best be understood by reference to FIGS. 2-6. As illustrated, the valve includes a generally disc-shaped inner housing 26 fashioned from a durable, biologically compatible material, such as thermoplastic polymers of polyethersulfone or polycarbonates. The inner housing 26 is received within an outer housing comprising two members 27 and 28 formed of silicone rubber or a similar material bonded together over the inner housing. The dimensions of the inner and outer housings are selected so as to be compatible with subcutaneous implantation of the valve over the cranium 29 (FIG. 1).

Figure 3:
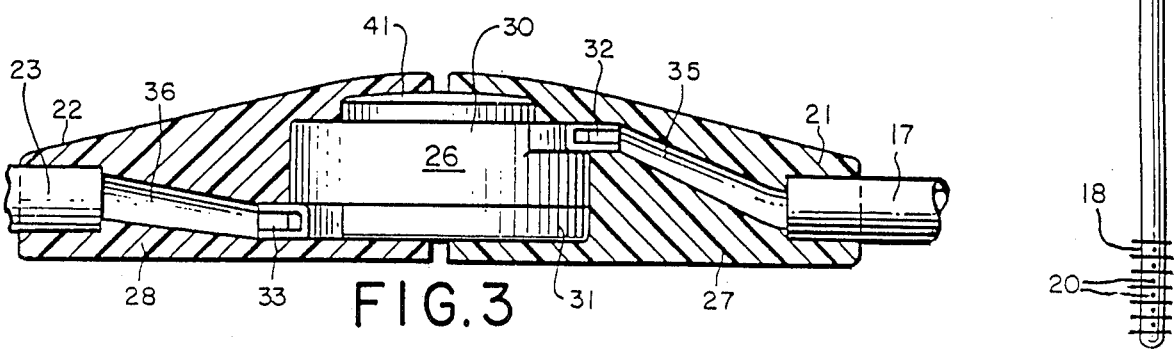
Figure 11:
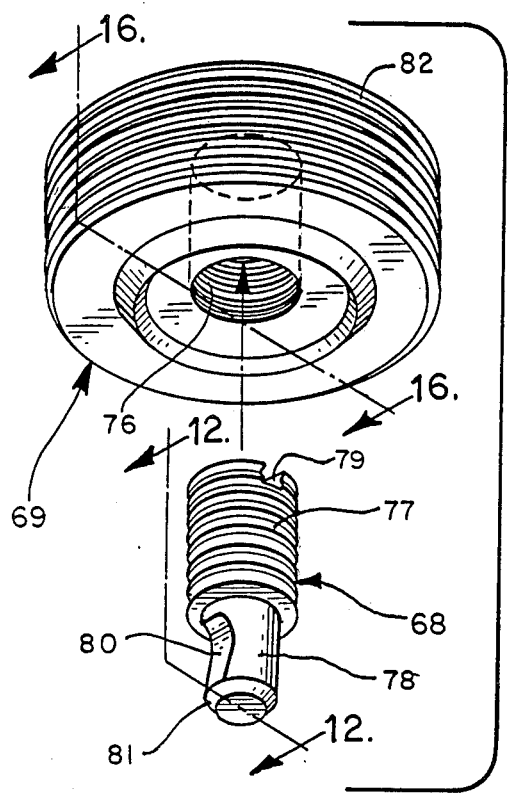

As is best illustrated in FIGS. 3 and 4, the inner housing 26 comprises two circular cup-shaped housing members 30 and 31. Housing member 30 includes an inlet port 32, and housing member 31 includes an outlet port 33, by means of which fluid can pass to or from the interior of the housing. In this regard, outer housing members 27 and 28 are provided with internal conduits 35 and 36, which provide fluid communication between inlet port 32 and outlet port 33, respectively.

Housing member 30 is provided with an aperture 37 through the upper surface thereof. As illustrated in FIG. 4, the aperture 37 includes a region 38 of relatively larger diameter coaxially aligned above a region of relatively smaller diameter 40. Both the relatively larger diameter and smaller diameter regions of the aperture are internally threaded as illustrated in order to seal the aperture while still allowing ready access to the interior region of the housing. The upper housing member 30 includes a removable cap 41 having a domed upper surface 42 and an externally threaded cylindrical lower portion 43 dimensioned to engage the threads of region 38 of aperture 37. To provide a tight seal between the cap and the housing, the upper housing member may include a raised annular seat 44 adjacent the periphery of the aperture against which the cap bears as it is turned into the upper housing member.

Referring to FIGS. 4 and 6, fluid control valve 12 includes partition means in the form of a diaphragm 45 which extends laterally across the interior region of the inner housing to divide that region into first and second interior chambers 46 and 47 (FIG. 6), respectively. The diaphragm 45 may be fashioned from a flexible biocompatible material, such as silicone rubber, and, as best seen in FIG. 4, may comprise a disc-shaped member having an aperture 48 provided centrally therethrough. The operative region 50 of the diaphragm is provided with an annular groove 51 concentrically aligned with the center aperture which allows the operative region to travel vertically in response to a pressure differential between the first and second interior chambers.

Toward its center, and in the region immediately surrounding the aperture, the thickness of diaphragm 45 is increased to form a hub region 52, having upper and lower portions 53 and 54, respectively. An annular channel 55 of rectangular cross-section is provided in the sidewall of aperture 48 between portions 53 and 54. Diaphragm 45 also includes an integrally formed rim portion 56 along its outer circumference which facilitates installation of the diaphragm in the housing.

When assembled, upper housing member 30 interlocks with lower housing member 31 by engagement of their corresponding edges. Diaphragm 45 is received in a space provided therebetween with its rim portion fixedly engaged by the two interior housing members. When mounted in this manner, the operative portion 50 of the diaphragm is free to move in response to a pressure differential existing between fluids contained in the first and second chambers.

To regulate the passage of fluids from the first chamber 46 to the second chamber 47, and hence from a brain ventricle to the drainage area of the body, the valve includes valving means for regulating fluid communication between the first and second chambers. These valving means include a valve seat 67 mounted for movement with diaphragm 45, a valve stem 68 mounted to coact with the valve seat, and a valve closure member 69 mounted to coact with the diaphragm.

Referring to FIGS. 4 and 6, the valve seat 67 is preferably in the form of a washer-shaped ring dimensioned to fit within the annular channel 55 provided in the central hub portion 52 of diaphragm 45, between portions 53 and 54. The valve seat defines a flow metering orifice 70 extending centrally through the diaphragm for establishing fluid communication between chambers 46 and 47. The diameter of the orifice is greater than the flow metering portion of the valve stem assembly 68, which extends through the orifice 70 of valve seat 67 as illustrated in FIG. 6. The valve seat is located directly beneath the valve stem so that a substantial part of the stem projects through orifice 70 during operation of the valve.

In accordance with the invention, the valve closure member 69 is seen to be of generally cylindrical form, having an annular valving portion 73 arranged to bear against hub portion 52 of diaphragm 45. Closure member 69 is provided with an internally threaded aperture 76 adapted to receive valve stem member 68, the latter being provided with a threaded shank portion 77 which is threadedly received within the aperture. The valve stem 68 further includes an intermediate fluid metering portion 78, a slotted head portion 79, and a frusto-conical end portion 81. The slotted head portion 79 is adapted to receive a suitable tool to threadedly advance or retract valve stem 68 through valve closure member 69.

As seen in FIG. 6, in an assembled condition, the valve stem 68 is threaded through the central aperture 76 of valve closure member 69. The fluid flow control portion 78 of the stem extends below the plane of the annular valving portion 73 of valve closure member 69, and the upper slotted head portion 79 of the stem member projects upwardly from the top surface of the closure member. The head portion 79 is accessible when the cap 41 is removed from the valve to permit the use of a suitable tool to advance or retract the stem member 68 relative to the closure member 68, thus permitting adjustment of the pressure and flow levels maintained by stem member 68 in conjunction with valve seat 67.

The valve closure member 69 is mounted within the lesser diameter portion 40 of aperture 37. To this end, the outer surface 82 (FIG. 4) of closure member 69 is externally threaded and dimensioned to engage the threads of portion 40. The closure member 69 may include a raised centrally located stem mounting portion 85 which includes aperture 76 through which the head portion 79 of valve stem 68 extends. The mounting portion 85 may also include a pair of opposed outwardly projecting lugs or ears 87 which can be engaged by a suitable tool received in an adjacent annular recess 84 so that the closure member 69 can be threadedly advanced or retracted within the upper housing member 30 relative to diaphragm 45 and valve seat 67 to adjust the closing pressure of the valve.

When no differential pressure acts on diaphragm 45, the top surface of the diaphragm contacts the portion 73 of valve closure member 69 and flow between chambers 46 and 47 is prevented. Adjustment of the pressure at which the valve opens is obtained by advancing or retracting valve closure member 69 within upper housing 30 relative to diaphragm 45. As the flow control portion 78 of the valve stem member 68 is received through the orifice 70 of valve seat 67, the sidewalls of the stem member 68 additionally function to align the valve seat to alleviate sticking problems between the stem and the valve seat due to the lack of concentricity. This nesting configuration thus aids in reducing cost of manufacture as well as permitting increased variation in functional characteristics of the valve.

Figure 9:
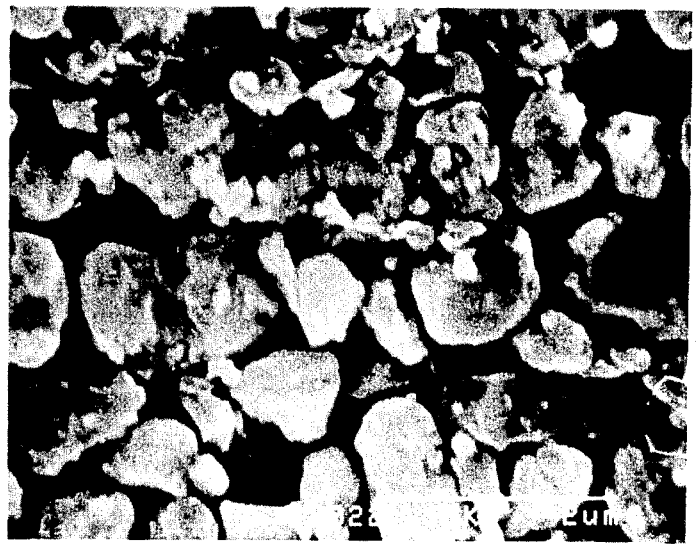

FIG. 6 illustrates the operation of the valve in the absence of a CSF pressure differential, or a less than minimum threshold or popping pressure, between chambers 46 and 47. FIGS. 7-9 illustrate the operation of the valve in response to various CSF pressure levels in excess of the minimum threshold pressure. FIG. 10 is a simplified graphical depiction of pressure vs. flow characteristics of the valve. Basically, once CSF pressure has exceeded a predetermined minimum level the fluid control valve 12 operates to maintain a predetermined differential pressure $P_1$ between fluid in the brain ventricle and fluid at the body drain location. The valve accomplishes this by adjusting the fluid flow rate Q through the valve so that the pressure $P_1$ is maintained. This operation of the valve is shown in region I of FIG. 10.

Should the differential pressure rapidly increase beyond a predetermined intermediate threshold level, such as when the patient stands, a CSF flow rate greater than a preselected maximum rate $Q_1$ would be necessary to maintain the desired pressure $P_1$. Since such a high flow rate would create the risk of hyperdrainage of the brain ventricle, the valve functions to maintain a relatively constant flow rate notwithstanding the increase in differential pressure, as depicted in region II of FIG. 10.

In a practical valve, the flow rate will not be entirely independent of the applied differential pressure but rather will increase from a lower flow rate $Q_1$ to a higher flow rate $Q_2$ as differential pressure increases between pressure $P_1$ and pressure $P_2$, as indicated by the solid line in FIG. 10. However, flow rates $Q_1$ and $Q_2$ are sufficiently low so that during a temporary rapid increase in differential pressure, pressure will return to normal before a quantity of CSF sufficient to cause adverse side effects flows through the valve. In a typical valve $Q_1$ and $Q_2$ may be 0.4 ml./min. and 0.8 ml./min., respectively, while pressures $P_1$ and $P_2$ may be 80 and 350 mm. of water, respectively.

While it is desirable to avoid high flow rates through the valve in order to avoid hyperdrainage of the ventricle, it may, under certain emergency conditions, be desirable to allow rapid shunting of CSF in order to avoid possible brain damage. When the valve is operating in region II, increases in differential pressure tend to close the valve. To avoid the possibility of building excessively high ventricular CSF pressure, the valve functions such that when differential pressure exceeds a maximum threshold level $P_2$, a fluid flow rate sufficient to maintain $P_2$ is established. This operation is depicted in Region III of FIG. 10. When the valve is operating in this region, further increases in differential pressure result in an increase in fluid flow through the valve, thereby stabilizing the pressure at slightly above $P_2$.

FIGS. 6-9 illustrate operation of the valve in the regions previously described. CSF applied to the inlet port 21 of the valve completely fills the first chamber 46 and exerts a downwardly directed force on the diaphragm 45 by reason of the CSF pressure within the brain ventricle. Since the second chamber 47 is in fluid communication with the selected drainage location in the body, the pressure of the CSF therein exerts an upwardly directed force on the lower surface of the diaphragm. Accordingly, the differential pressure between CSF in the brain ventricle and fluid at the drainage location results in vertical deflection of both the diaphragm and the valve seat 67 carried thereon.

As shown in FIG. 6, when differential pressure is negative or non-existent, or below the minimum threshold level of the valve, valve seat 67 contacts the annular valving portion 73 of valve closure member 69 and flow through orifice 70 is prevented. As shown in FIG. 7, when the differential pressure is relatively low but in excess of the threshold pressure resulting from the biasing of diaphragm 45 against valving portion 73, a slight downward displacement of the diaphragm occurs sufficient to displace valve seat 67 from the valving portion 73, thereby allowing CSF to pass through orifice 70 from chamber 46 to 47. As the pressure increases, the displacement of the diaphragm increases, causing a flow increase. Thus, the valve maintains a predetermined pressure differential $P_1$, as called for in Region I operation.

The bottom portion 78 of valve stem 68, which defines the fluid flow control and restrictor portion 78, is dimensioned so as to barely pass through the orifice 70 of valve seat 67. By way of example, in one embodiment of the valve, the valve seat orifice has a diameter of 0.030 inches at its narrowest point and the clearance between the restrictor portion of the valve stem and the orifice at the narrowest point is on the order of 0.001 of an inch.

Figure 12:
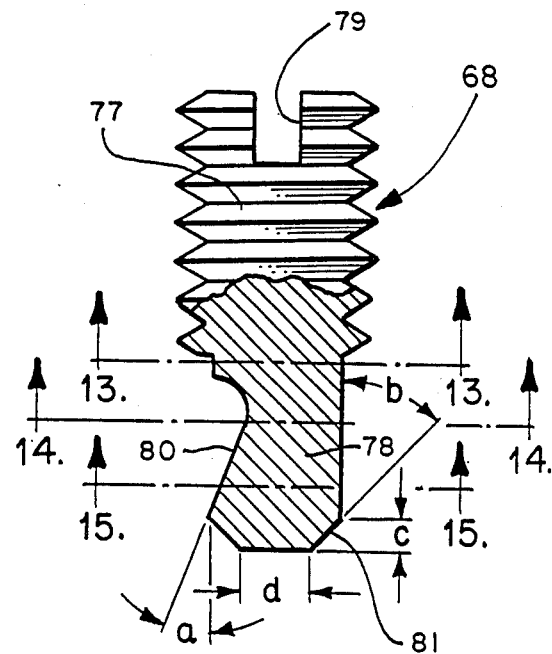
Figure 13:
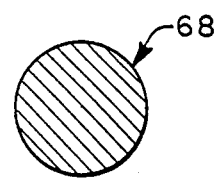

As illustrated in FIGS. 11-15, the flow control portion 78 of the valve stem member 68 is generally cylindrical and includes a metering notch 80 of progressively reduced depth in the direction of fluid flow. As shown in FIG. 12, the notch 80 may be formed at an angle a relative to the axis of the stem, thereby providing the progressively decreasing depth. The frusto-conical end portion 81 is formed on the stem by an annular rim portion inclined at an angle b to the axis to provide a flat end surface of reduced diameter d.

Figure 14:
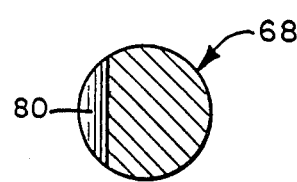
Figure 15:
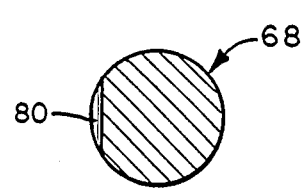
Figure 16:
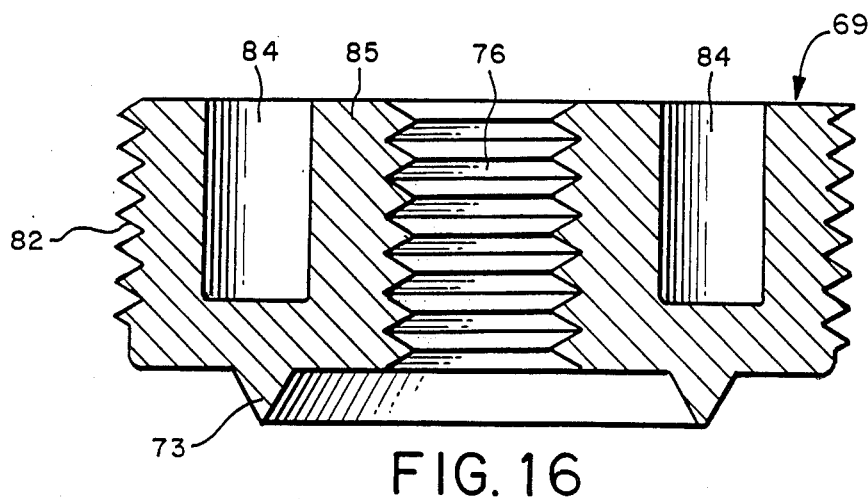

As shown by FIGS. 14-15, the effect of metering notch 80 is to progressively reduce as differential pressure increases, the portion of orifice 70 available for fluid flow. This provides the Region II constant flow valving condition illustrated in FIG. 8. When a sudden increase in differential pressure occurs, and the pressure differential exceeds pressure $P_1$, the downward displacement of diaphragm 45 causes valve seat 67 to descend over metering portion 78 allowing flow to occur through orifice 70 by way of metering notch 80. Since the depth of the notch decreases with increased deflection of the diaphragm, the higher flow rate ordinarily resulting from increased pressure is offset by a more restricted flow path, so that a relatively uniform rate of fluid flow occurs between the chambers despite differential pressure increases.

FIG. 9 illustrates operation of the valve in region III of FIG. 10, such as would occur when the differential pressure exceeds a predetermined pressure level $P_2$. In this condition, differential pressure displaces the diaphragm to a degree sufficient to cause valve seat 67 to move beyond the bottom portion 81 of valve stem 68 so as to allow CSF to flow past the aforesaid bottom portion and through orifice 70. Further increases in differential pressure cause the valve seat to be further displaced away from valve stem 68 thereby further opening orifice 70 and allowing a still greater fluid flow rate. Thus, the valve operates as a pressure regulating device, increasing flow to counteract pressure increases, and the predetermined maximum pressure $P_2$ is maintained.

Valve closing pressure (minimum pressure level) and the point of greatest flow restriction (maximum pressure level) can be set independently by adjustment of valve closure member 69 and valve stem 68, and the length between the flow control surface 73 and the point of greatest fluid flow restriction is not a design limitation. By reason of the two adjustments, variations in physical properties of diaphragms can be accommodated.

Manufacturing techniques are less exacting and costly by reason of the cylindrical valve stem construction, wherein a single notch, which can be readily and accurately machined by conventional milling techniques provides a precision metering orifice for flow control. This avoids the multiple diameter pin constructions of previous valve designs, which could only be formed by multiple step techniques at substantial expense. Furthermore, the annular valve closure member 69, by reason of its 360° circumferential metering surface 73, provides positive fluid control between valve closed and open states with only limited movement of diaphragm 45, thereby allowing the valve to be constructed with minimum thickness.

Conventional materials may be used in constructing pressure relief valve 12. For example, the valve stem 68, and valve seat 67 may be formed of synthetic sapphire material. Valve closure member 69, and the housing may be formed from a biocompatible polycarbonate material and diaphragm 45 may be formed from a silicone material.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A valve for controlling the passage of body fluids from one location in the body to another location, comprising:
   a housing having first and second interior chambers;
   inlet port means for establishing fluid communication between said first chamber and the one location;
   outlet port means for establishing fluid communication between said second chamber and the other location;
   partition means in said housing separating said first and second chambers and being movable in response to fluid pressure differential therebetween;
   a valve seat forming part of said partition means and defining a fluid flow orifice to permit flow of fluid between said chambers;
   a valve closure member including an annular valving surface in said first chamber for engaging said partition means in registry with and surrounding said orifice to prevent flow through said orifice when said pressure differential falls below a predetermined minimum level; and
   a valve stem extending from said valve closure member and through said orifice into said second chamber, said valve stem including a flow metering surface which coacts with said valve seat to meter said fluid flow through said orifice as a function of the position of said partition means when said pressure differential exceeds said predetermined minimum level.

2. A valve as defined in claim 1 wherein the position of said valve closure member is adjustable relative to said partition means to vary said predetermined minimum pressure level.

3. A valve as defined in claim 2 wherein said housing includes a first movable member to which is attached said valve closure member and which provides for adjustment thereof; and
   a second movable member forming a part of said valve stem for adjustment thereof, both said first and second movable members being accessible externally of said housing for independent adjustment thereof.

4. A valve as defined in claim 2 wherein said valve closure member is provided with an aperture, said aperture receiving a portion of said valve stem whereby the position of said valve stem can be adjusted relative to said valve closure member.

5. A valve as defined in claim 1 wherein the positions of said valve stem and said valve closure member are independently adjustable within said housing.

6. In an intracranial pressure regulator valve adapted for transfer of cerebrospinal fluid from one location to another, said regulator valve including first and second fluid handling chambers separated by a flexible biocompatible diaphragm which retains a valve seat having a flow metering orifice, the improvement comprising:
   a valve closure member including an annular valving surface in said first chamber for engaging the diaphragm in registry with and surrounding said orifice to prevent flow through said orifice when said pressure differential falls below a predetermined minimum level, said valve closure member being in combination with a valve stem extending from said valve closure member and through said orifice into said second chamber, said valve stem including a flow metering surface which coacts with said valve seat to meter the flow of fluid through said orifice as a function of the position of said diaphragm.

7. A valve as defined in claim 6 wherein the positions of said valve stem and said valve closure member are independently adjustable within said housing.

8. A valve for controlling the passage of body fluids from one location in the body to another location, comprising:
   a housing having first and second interior chambers;
   inlet port means for stabilizing fluid communication between said first chamber and the one location;
   outlet port means for establishing fluid communication between said chamber and the other location;
   valving means between said first chamber and said second chamber for regulating fluid flow between said first and second chambers, said valving means including a valve closure member, a valve seat defining a flow metering orifice and a valve stem extending through said orifice and providing a first condition in which fluid flow between said first and second chambers is prevented, a second condition in which fluid flow between said first and second chambers is sufficient to maintain a first substantially constant predetermined pressure differential between first and second chambers a third condition in which fluid flow between said first and second chambers is of a substantially constant rate, and a fourth condition in which fluid flow between said first and second chambers is sufficient to maintain a second substantially constant predetermined pressure differential between said first and second chambers;

partition means in said housing including a diaphragm separating said first and second chambers and movable in response to the pressure differential therebetween, said valve seat being carried on said diaphragm and being operatively associated with said valve closure member and said valve stem such that the flow of fluid between said first and second chambers is sequentially conditioned by a staged displacement of said partition means from said closure member from said first condition through said second and third conditions to said fourth condition whereby in response to an increasing pressure differential between said first and second chambers said valving means sequentially prevents the passage of fluids between the one location and the other location, maintains a constant fluid pressure differential between said first and second chambers maintains desired constant rate of fluid flow between the one location and other location, and maintains a second constant fluid pressure differential between said first and second chambers; and wherein said valve closure member includes a generally annular valving surface for engaging said diaphragm in registry with and surrounding said orifice to prevent fluid flow through said orifice when said differential pressure falls below a predetermined minimum level, said valve closure member being in combination with said valve stem and extending from said valve closure member and through said orifice into said second chamber, said valve stem including a flow metering surface which coacts with said valve seat to meter the flow of fluid through said orifice as a function of the position of said diaphragm.

9. A valve as defined in claim 8 wherein the position of said valve closure member is adjustable relative to said partition means to vary said predetermined minimum pressure level.

10. A valve as defined in claim 9 wherein said housing includes a first movable member to which is attached said valve closure member and which provides for adjustment thereof; and a second movable member forming a part of said valve stem and which provides for adjustment thereof, both said first and second movable members being accessible externally of said housing for independent adjustment thereof.

11. A valve as defined in claim 8 wherein said housing includes a first movable member to which is attached said valve closure member and which provides for adjustment thereof; and a second movable member forming a part of said valve stem and which provides for adjustment thereof, both said first and second movable members being accessible externally of said housing for independent adjustment thereof.

12. A valve as defined in claim 6 wherein the positions of said valve stem and said valve closure member are independently adjustable within said housing.

13. A valve as defined in claim 9 wherein said valve closure member is provided with an aperture, said aperture receiving a portion of said valve stem whereby the position of said valve stem can be adjusted relative to said valve closure member.

* * * * *

2.0μm - 3.0μm SiAlON